(12) United States Patent
Zhou et al.

(10) Patent No.: US 10,946,039 B2
(45) Date of Patent: Mar. 16, 2021

(54) CHITOSAN ACRYLIC ACID DERIVATIVE HEMOSTATIC POWDER

(71) Applicants: Jiangsu NewValue Medical Products Co., Ltd., Jiangsu (CN); Shanghai NewValue Medical Products Co., Ltd., Shanghai (CN)

(72) Inventors: Yingshan Zhou, Jaingsu (CN); Rui Jiang, Jaingsu (CN); Zuguang Gong, Jaingsu (CN); Liqin Xu, Jaingsu (CN); Shiming Zhou, Jaingsu (CN); Xiaoming Zhou, Jaingsu (CN)

(73) Assignees: Jiangsu NewValue Medical Products Co., Ltd., Taizhou (CN); Shnaghai Newvalue Medical Products Co., Ltd., Shanghai (CN)

( * ) Notice: Subject to any disclaimer, the term of this patent is extended or adjusted under 35 U.S.C. 154(b) by 30 days.

(21) Appl. No.: 16/343,887

(22) PCT Filed: Oct. 25, 2017

(86) PCT No.: PCT/CN2017/107634
§ 371 (c)(1),
(2) Date: Apr. 22, 2019

(87) PCT Pub. No.: WO2018/077183
PCT Pub. Date: May 3, 2018

(65) Prior Publication Data
US 2020/0306287 A1 Oct. 1, 2020

(30) Foreign Application Priority Data
Oct. 26, 2016 (CN) .......................... 201610969448.3

(51) Int. Cl.
*A61K 31/722* (2006.01)
*A61P 7/04* (2006.01)
*A61K 9/16* (2006.01)

(52) U.S. Cl.
CPC .............. *A61K 31/722* (2013.01); *A61K 9/16* (2013.01); *A61P 7/04* (2018.01)

(58) Field of Classification Search
CPC ............ A61K 31/722; A61K 9/16; A61P 7/04
See application file for complete search history.

(56) References Cited

U.S. PATENT DOCUMENTS

2009/0109820 A1    4/2009   Morikawa et al.

FOREIGN PATENT DOCUMENTS

| CN | 1589912 A | 3/2005 |
| CN | 101037486 A | 9/2007 |

(Continued)

OTHER PUBLICATIONS

Bennet et al, Review of New Topical Hemostatic Dressings for Combat Casualty Care, Military Medicine, 179, 5:497 (Year: 2014).*

*Primary Examiner* — Carlos A Azpuru
(74) *Attorney, Agent, or Firm* — Abelman, Frayne & Schwab; Stefan Knirr (57) ABSTRACT

The present invention provides a hemostatic powder. The hemostatic powder is mainly present in the form of a columnar particle, wherein the ratio of axial length to diameter of the columnar particle is less than 5; the hemostatic powder includes a polymer represented by the following structural formula:

(Continued)

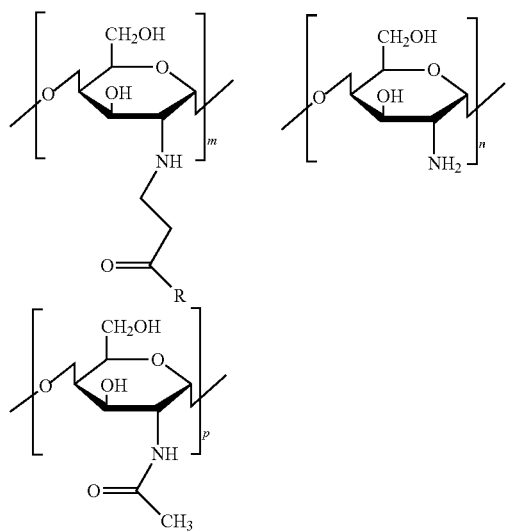

wherein the R is at least one selected from the group consisting of $-NH_2$, $-OCH_2CH_2OH$, $-OCH_2CH_2CH_2OH$, $-OH$, $-ONa$, $-OK$ and $-OCa$; m, n and p respectively represent number percentages of corresponding repeating units in polymer molecules, and satisfy the following equations: $m+n+p=1$, $p/(m+n+p)=0.05~0.30$; the substitution degree D is defined as $=m/(m+n+p)$, the overall substitution degree of the columnar particle is defined as Ds, the substitution degree of the polymer at the center point of the cross section of the columnar particle is defined as Do, and the substitution degree of the polymer at the edge of the cross section of the columnar particle is defined as Dx, and the following equations are satisfied: $Ds=0.09~0.8$, $Do/Dx=0~0.7$.

16 Claims, 2 Drawing Sheets

(56) References Cited

FOREIGN PATENT DOCUMENTS

| | | | | |
|---|---|---|---|---|
| CN | 101368328 | A | | 2/2009 |
| CN | 102008742 | A | | 4/2011 |
| CN | 102137684 | A | * | 7/2011 |
| CN | 102727925 | A | * | 10/2012 |
| CN | 102727929 | A | | 10/2012 |
| CN | 103255615 | A | | 8/2013 |
| CN | 103910894 | A | | 7/2014 |
| CN | 106192390 | A | * | 12/2016 |
| CN | 106215219 | A | | 12/2016 |
| CN | 106267305 | A | | 1/2017 |
| CN | 106390184 | A | | 2/2017 |
| EP | 0199531 | B1 | | 4/1991 |
| KR | 20140114083 | A | | 9/2014 |

* cited by examiner

CHITOSAN ACRYLIC ACID DERIVATIVE HEMOSTATIC POWDER

FIELD OF THE INVENTION

The present invention relates to a hemostatic powder, and in particular to a hemostatic powder capable of absorbing liquid by swelling, wherein the hemostatic powder at least contains columnar particles.

BACKGROUND OF THE INVENTION

Hemostatic powder is a common medical material and is meant to be quickly scattered on large-area or irregular wounds to quickly stop bleeding, which is easier and faster than pasting, dressing and the like. For example, in the case of major trauma such as severe burns, the wound area is large and the shape is irregular. Meanwhile, since a patient loses most of the skin on the body surface, obvious pain will be brought in the dressing process. The hemostatic powder itself is free from the possibility of causing the above defects and can be quickly scattered on the wound in the first time without being affected by the shape or area of the wound, so that the timing of treatment is not delayed, and the pain of the patient can also be reduced. In addition, for internal bleeding caused by spontaneous bleeding, trauma or surgery, such as visceral bleeding of liver and kidney and the like, because the wound is deep inside the body, it is difficult to dress in the traditional manner, and it is even difficult to plug a small amount of hemostatic fiber agglomerates. If hemostatic powder is used, however, it can be easily sprayed onto the wound to solve the problem of hemostasis on a specific part. Moreover, as a powder particle, the hemostatic powder has a large specific surface area while contacting the wound, so that the effect is better than other forms under the same dosage. Furthermore, the hemostatic powder can be quickly degraded in vivo after the healing of the wound, thereby overcoming the shortcoming that the traditional dressing material adheres to the wound and is difficult to remove. Therefore, the hemostatic powder has a wide application space for both internal bleeding and trauma.

Most of the hemostatic powders on the market are made by grinding traditional Chinese medicine into powder, and some microporous materials are used. Meanwhile, traditional synthetic hemostatic materials (such as fibers) can also be pulverized. For example, in order to stop bleeding and absorb wound exudate at the same time, the hemostatic powder can be prepared from microporous material. For example, Chinese patent document CN102178691 A discloses a microporous starch for hemostasis, and Chinese patent document CN101703519A discloses a special zeolite powder, and so on. However, the preparation of the microporous material is relatively complicated. From the viewpoint of simplifying the process and reducing the cost, the conventional medical fibers for wound care can also be pulverized into powder to prepare the hemostatic powder. For example, Chinese patent document CN101543640A discloses such technology, but ordinary fiber-like materials naturally have the possibility of adhering to wounds, which may hinder the treatment and cause pain to the patient, so that other additives need to be added to deal with this matter. In this case, the additives, will increase the cost and may cause other side effects. Therefore, more suitable fiber materials are always being developed in the art.

Usually, during the preparation of the hemostatic powder, the raw material is modified. The raw material can be directly modified before the hemostatic powder is prepared, or the powder can be directly modified after the powder is prepared. As the raw material of the hemostatic powder, for example, chitin has good biocompatibility, biodegradability, performance on hemostasis and promotion of wound healing and the like, so that the chitin has a wide application prospect in various tissue engineering scaffold materials such as absorbable surgical sutures, wound dressings, drug carrier materials, artificial skin, etc.

The chitin becomes a viscous colloid when dissolved in an organic acid or an inorganic acid, and chitin fibers for preparing the wound dressings can be prepared by spinning, solidifying, washing, drying and other procedures. Chinese patent document CN1129748A (deacetylated chitin fiber and manufacturing method and application thereof), Chinese patent document CN1149093A (chitin fiber and preparation method thereof), Chinese patent document CN101250759A (medical chitosan fiber and preparation method thereof) and the like successively disclose the manufacturing method of the chitin fibers. However, the chitin fibers prepared by these methods have defects such as weak antibacterial property and poor liquid absorption in medical clinical applications, and the effect is not ideal when being applied to the treatment of burn or scald wounds which are easily infected or have large amount of exudate, and of chronic healing wounds such as pressure ulcer.

In order to improve the liquid absorption property of the chitin fibers, chemical modification methods are widely used. For example, the chitin fibers are alkalized and then modified into carboxymethyl chitin fibers and the like by chloroacetic acid, in Chinese patent document CN1715465A (carboxymethyl chitosan fiber and preparation method and application thereof). The chitin fibers are alkalized and then modified into hydroxyethyl chitin fibers by ethylene oxide, and the literature on this aspect also includes Chinese patent document CN101368328A (a preparation method of hydroxyethyl chitosan fiber) and the like. However, these modification methods, on one hand, are harsh in reaction conditions, cumbersome in steps and are difficult to control; and on the other hand, the positions and numbers of substituents on molecular chains of a reaction product are uncertain, such that the liquid absorption property of the product is difficult to be effectively controlled. In addition, the above product has no antibacterial property. These problems will greatly limit the application of dressings prepared from the chitin fibers in clinical, especially burn or scald wounds and chronic wound treatment.

In particular, in the conventional chitin fibers, people often control the liquid absorption properties of the fibers by controlling the degrees of substitution, but the inventors of the present invention have found that if the substitution degree is too low, the liquid absorption amount of the fiber is insufficient, and if the substitution degree is too high, although the liquid absorption amount is significantly increased, the fiber shape is difficult to maintain, that is, the fiber is dissolved or dispersed by the absorbed liquid. At this time, the outflow of the liquid causes a certain degree of loss of the liquid absorption function.

With respect to the hemostatic powder obtained by pulverizing the fiber, most of the advantages and disadvantages are similar to those of the fiber materials. Although the requirements of the powder on shape maintenance are not as high as the fiber itself, there are still many rooms for improvement. Moreover, the process for producing the hemostatic powder by pulverizing or cutting fiber is simple, does not bring an excessive cost burden, and can better retain the property of the fiber to absorb liquid by swelling, and can also obtain the advantages of anisotropic liquid absorption by swelling of the powder.

SUMMARY OF THE INVENTION

In order to solve the above problems, the inventors of the present invention have conducted intensive research, and surprisingly found that by controlling the proportion of repeating units having different substituent groups in a polymer contained in the particles of the hemostatic powder and making the substitution degree of the outer side (edge) of the particle be greater than the substitution degree of the inside (center) of the particle, the particle can not only maintain good shape, but also can maintain sufficient liquid absorption capacity, so that the antibacterial and liquid absorption properties of the particle can be improved, particles suitable for clinical application are provided, especially applications in the aspects of hemostasis, burns, scalds, chronic wound treatment and the like.

Moreover, the inventors have found that for the chitin fibers, if the chitin fibers are modified and then pulverized to prepare the hemostatic powder, not only most of the original properties in the fiber state remain, but also, new advantages as powder particles also appear.

Specifically, the present invention is achieved by the following technical solutions:

The present invention relates to a hemostatic powder which is mainly present in the form of a columnar particle, the axial length/diameter of the columnar particle is less than 5;

the hemostatic powder contains a polymer represented by the following structural formula:

wherein
R is at least one moiety selected from the group consisting of —$NH_2$, —$OCH_2CH_2OH$, —$OCH_2CH_2CH_2OH$, —OH, —ONa, —OK and —OCa;
m, n and p respectively represent number percentages of corresponding repeating units in polymer molecules, and satisfy the following equations:

$$m+n+p=1,$$

$$p/(m+n+p)=0.05\sim 0.30;$$

the substitution degree D is defined as $=m/(m+n+p)$, the overall substitution degree of the columnar particle is defined as Ds, the substitution degree of the polymer at the center point of the cross section of the columnar particle is defined as Do, and the substitution degree of the polymer at the edge of the cross section of the columnar particle is defined as Dx, and the following equations is satisfied:

$$Ds=0.09\sim 0.8,$$

$$Do/Dx=0\sim 0.7.$$

The effects of the present invention are as follows:
(1) The hemostatic powder of the present invention can be directly prepared by cutting and pulverizing fibers, the fibers can be prepared only by ordinary solution modification (for example, embodiment 1) without using expensive raw materials or instruments, and without violent reaction conditions and the like. In other words, the particles of the liquid absorption hemostatic powder can be prepared by a simple and convenient process, mild reaction conditions, and a relatively low cost.
(2) The obtained hemostatic powder has good liquid absorption properties and antibacterial properties. The modification of the present invention does not affect the original antibacterial and liquid absorption properties of chitin, and on this basis, the surface modification degree of the particle is greater than the modification degree of the central part while being modified in the manner satisfying the above conditions. During liquid absorption, the modification degree of the central part is small, the liquid absorption amount is reduced, it is not easy to dissolve, the molecular shape is strictly maintained, and it acts as a "skeleton", while the edge part still maintains a larger degree of modification and liquid absorption amount. Meanwhile, the outside of the particle can be well attached to the skeleton of the central part by the intermolecular force, and the structure will not fall apart due to dissolution even after the liquid absorption amount is increased. Accordingly, the obtained particles can maintain a good shape after a large amount of liquid absorption, that is, the swelling degree is large, and it is not easy to be dissolved by the absorbed liquid, at this time, the absorbed liquid is locked in the particle, and the phenomenon that the original structure falls apart due to excessive dissolution of the particle after excessive liquid absorption, such that the absorbed liquid is released from the particle, does not occur.
(3) During the liquid absorption, the "skeleton" of the central part hardly swells, thereby maintaining the original length, and thus the external structure of the particle attached to the skeleton is difficult to elongate due to the restriction of the skeleton during liquid absorption. Therefore, when the obtained particle becomes swollen by the liquid, the particle only swells along the radial direction of the particle as much as possible to become thick. That is, the particle is neither stretched or lengthened through the liquid absorption, nor uniformly swollen along various directions.

In particular, while serving as the hemostatic powder, the particle becomes a gel after liquid absorption, and can keep a good shape while absorbing a large amount of liquid. Furthermore, particles mainly swell along the radial direction rather than the longitudinal direction, so that the particles basically become flattened and have a larger area, In this way, the contact area with the wound is greatly expanded after being sprayed onto the wound, and the particle can be better attached to the wound, thereby playing a better wound hemostatic role. In addition, the hemostatic powder particles have certain anisotropy, and different hemostatic powder particles have different swelling directions during swelling, which is advantageous for quickly sealing the wound to play a hemostatic role.

In addition, since the surface of the polymer contains an amino group having positive charges, it can adsorb red blood cells and platelets having negative charges. Meanwhile, in cooperation with the large specific surface area of the bottom surface of the cake-like powder after the liquid absorption, the red blood cells and platelets can be easily gathered in the area so as to trigger coagulation process, improve the hemostasis effect and reduce the time required for hemostasis.

BRIEF DESCRIPTION OF THE DRAWINGS

The letters in FIG. 2 and FIG. 3 express the following meanings:
"a" represents an unmodified raw material fiber; "b-g" represent raw material fibers in embodiment 1 to embodiment 6, subscripts 1 and 2 respectively represent shapes before and after the liquid absorption (for example, "$a_1$" represents the shape before the liquid absorption of the raw material fiber, "$a_2$" represents the shape after the liquid absorption of the raw material fiber, and so on).

DETAILED DESCRIPTION OF THE EMBODIMENTS

Figure 1:
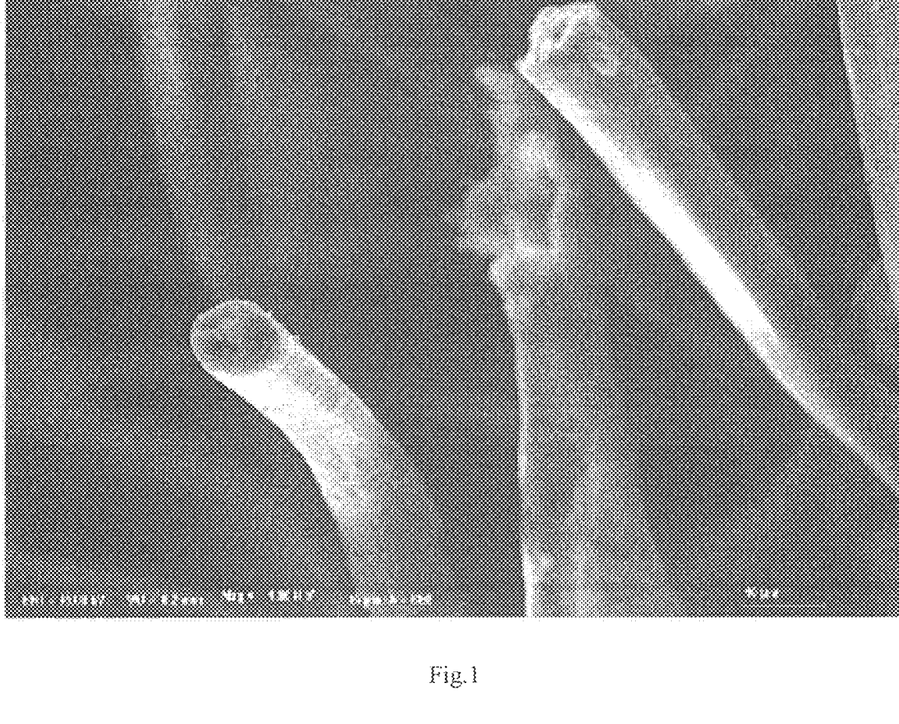
FIG. 1 is a micrograph showing a raw material fiber microstructure of the present invention.
Figure 2:
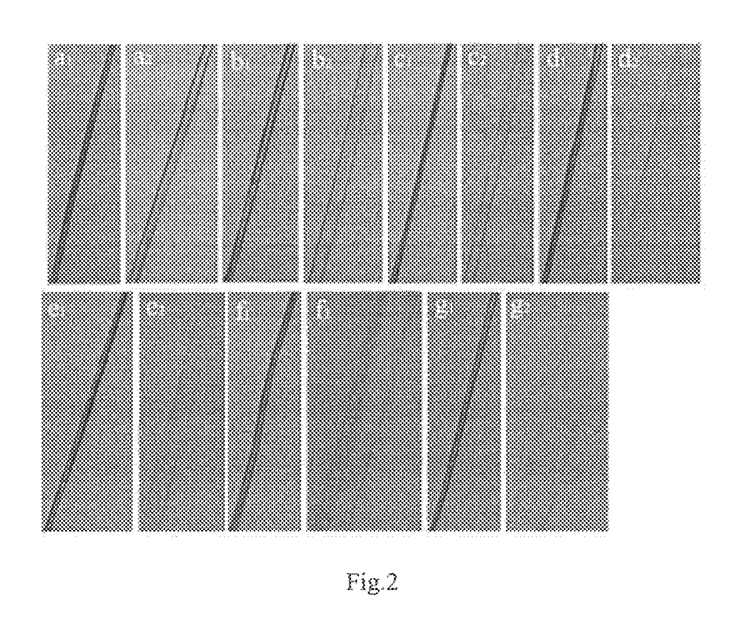
FIG. 2 is a schematic diagram showing the shape and structure of raw material fibers having different degrees of substitution of the present invention after liquid absorption. Specifically, a single raw material fiber is placed in 0.9% physiological saline at 37° C. for 30 min and is taken out to be fixed on a glass slide, and the shape change of the raw material fiber after liquid absorption is observed under an optical microscope.
Figure 3:
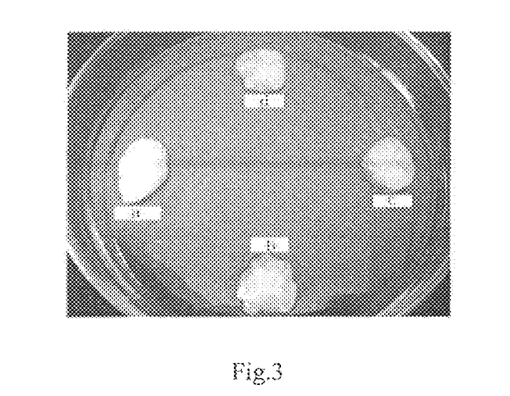
FIG. 3 is a schematic diagram showing the shape and structure of a raw material fiber bundle of raw material fibers with different degrees of substitution of the present invention. Specifically, the raw fiber bundle is placed in 0.9% physiological saline at 37° C. for 30 min to observe the shape change of the raw material fiber bundle after liquid absorption.

The solutions and effects of the present invention will be further described in detail below through preferred embodiments and examples, but the present invention is not limited by the following embodiments or examples.

As described above, in the conventional chitin fiber, if the substitution degree is controlled to control the liquid absorption property of the fiber, the following problems occur. That is, if the substitution degree is too low, the liquid absorption amount of the fiber is insufficient, and if the substitution degree is too high, although the liquid absorption amount is significantly increased, the fiber shape is difficult to maintain. That is, the fiber is dissolved or dispersed by the absorbed liquid.

For example, when the fiber in the following table is immersed in physiological saline, when the liquid absorption amount is measured in multiples of the dry weight of the fiber, when the substitution degree is relatively low, the liquid absorption amount is small, and the practical value is small, and when the substitution degree is too large, the fiber suffers excessive liquid absorption, thus losing the original structure, the originally absorbed water returns to the environment, and the liquid absorption amount cannot be measured.

| Substitution degree | 0.02 | 0.1 | 0.7 |
|---|---|---|---|
| Liquid absorption amount (multiple) | 0.5 | 1.0 | Cannot be measured |
| Shape after liquid absorption | Maintained | Maintained | Cannot be maintained |

In view of this, the inventors of the present invention surprisingly found that if the substitution degree of the central part of the fiber is reduced to maintain a good shape, and then the external structure of the fiber is attached to the skeleton by intermolecular forces, so that the fiber is unlikely to fall apart or disperse, and the basic fiber shape can still be maintained after a large amount of liquid absorption, thus achieving the present invention.

The inventors have also found that it is very convenient to cut or to pulverize the fiber to serve as a hemostatic powder.

The hemostatic powder of the present invention can be used as the hemostatic powder by making a polymer into the fiber, modifying the fiber and then pulverizing or cutting the fiber into a suitable size. However, the present invention is not limited to such method. For example, a block polymer or polymer powder can be subjected to the following method of solution modification of the fiber, but since the block polymer is not easy to be directly modified into the required gradient distribution through a simple and convenient solution method, and the powder size is small, the modification range is not easy to control, and the yield of qualified hemostatic powder particles is low. Therefore, it is preferred to make the polymer into the fiber with the suitable size at first, and then to perform the solution modification.

The reason why the hemostatic powder of the present invention is preferably a columnar particle is that it is equivalent to cutting off a section along the cross section of the fiber, therefore when such columnar particle serves as the hemostatic powder, its chemical properties are the same as those of the modified fiber. In practice, when the fiber is pulverized or cut, the direction does not need to be set very accurately. Due to the influence of the long strip shape of the fiber itself, even if the fiber is randomly pulverized by a common gas pulverizer, a large part of particles maintain a columnar shape or a shape approximate to it, the original performance will not greatly affected, while other fiber fragments do not necessarily maintain complete columnar shapes, but the overall performance is partially maintained with the degree of the shape, therefore, although the columnar particle theoretically has the best hemostatic effect, for the convenience of the process, it is not necessary to specifically cut the fiber in a precise orientation.

For example, after random pulverization and cutting, when observed under a microscope, the fiber mainly has the following several morphologies:
(i) a relatively complete columnar fiber, that is, a columnar or substantially columnar profile (including a curved columnar shape) discernible to a naked eye;
(ii) a very tiny fiber fragment by which the shape of the powder cannot be distinguished;
(iii) a small and medium-sized particle formed by mutual attraction and gathering of (ii), and the size of which is slightly greater than the diameter of the columnar particle; and (iv) an apparently larger particle formed by the mutual attraction and gathering between (i) and (ii), the size of which is significantly greater than the diameter of the columnar particle (i), that is, the columnar particle is used as the skeleton, the aggregated particle is significantly greater than the particle directly aggregated by micropowder, at this time, the columnar particle may be curved therein, and a plurality of columnar particles may even be entangled to form a skeleton structure so as to form a larger particle. For example, when two or more columnar particles form the skeleton structure together, some microparticles (ii) are agglomerated at the outside of the skeleton of the columnar particles, and some microparticles (ii) are wrapped inside the skeleton of the columnar particles.

Both (i) and (iv) can show the distribution advantage of the degrees of substitution of the columnar particles of the present invention, and although the shapes are difficult to recognize in (ii) and (iii), a certain proportion of the powder completely or partially maintain the distribution of the degrees of substitution required by the present invention.

During the precise orientation cutting, although the hemostatic powder can have a greater proportion of the above-mentioned particles (i), this cutting mode is low in efficiency; preferably, a pulverizing cutting mode with higher efficiency is adopted, for example, airflow pulverizing cutting, the proportion between the above particles (i) to (iv) can be changed by controlling the size of the airflow, but more preferably, the above-mentioned particles (i) to (iv) are separated by using a sieve.

In practice, after the pulverizing cutting, when the requirement for the liquid absorption property is high (for example, internal bleeding, and there is not much space near the wound to spray a large amount of hemostatic powder), the above smaller particles (ii) and a part of particles (iii) can be removed by screening, so that most of the hemostatic powder is the particles (i) and (iv), and at this time, the sieved particles can be used as ordinary hemostatic powder. In a use environment in which the requirement for the liquid absorption property is not critical (for example, external bleeding, even if a large amount of hemostatic powder is used, the convenience of treating the wound is not affected), the unsieved pulverized particles can be directly used.

Preferably, the columnar particle contained in the hemostatic powder has an axial length/diameter of less than 5, more preferably 3 or less, more preferably 1.5 or less and more preferably 1.2 or less. If the particle is too long, it is inconvenient to spray to the wound as powder and they tend to overlap or lap with each other, so that the effect of the relatively large specific surface area of the powder cannot be further improved. When the particle is too small, it is difficult to use the distribution of the degrees of substitution to maintain the shape. In view of the fact that a not too fine powder is obtained by the normal polymer preparation process or fiber pulverization process. Thus a lower limit does not need to be specifically set during the preparation. However, it is preferred that the column height/diameter is not less than 0.2, more preferably not less than 0.5 and more preferably not less than 0.8.

At this time, the ratio of the axial length to the diameter of the hemostatic powder is preferably close to 1:1 (i.e., the particle is close to a sphere or a cube and the like), for example, 0.8:1 to 1:0.8, more preferably 0.9:1 to 1:0.9, and most preferably 1:1.

In the present invention, for the columnar particle, the axial length means the length of the central axis of the columnar particle, that is, the length of the axis perpendicular to the cross section. The center of the cross section is located on said axis.

If the powder deviates from the spherical shape (i.e., when it is slender), or if the direction of the axial length happens to be the radial direction of the cross section of the polymer fiber, the powder particle will swell along the axial length after absorbing liquid to become very slender instead of becoming a wide and large cake shape, then it is difficult to attach the wound or gather the red blood cells/platelets by the bottom surface thereof, so that the hemostatic effect deteriorates. In this case, some of the properties functions of the hemostatic powder is decreased, so that the required dosage increases, which not only increases the use cost, but also leads to excessive time required for degradation in vivo, which is not conducive to wound healing.

The particle diameter of the hemostatic powder of the present invention is preferably 0.2-1000 µm, the lower limit is more preferably 0.3 µm, more preferably 1 µm, more preferably 5 µm and most preferably 10 µm, and the upper limit is preferably 600 µm, more preferably 300 µm, even more preferably 100 µm and most preferably 50 µm.

When the particle diameter of the hemostatic powder is too large, the specific surface area is correspondingly reduced, and the liquid absorption area or the contact area with the wound is also reduced, which is not conducive to hemostasis performance. However, when the particle diameter is too small, the original shape of the fiber as powder is more difficult to maintain, instead it might be dissolved in the liquid, resulting liquid absorption failure.

The bulk density of the hemostatic powder is preferably 0.5-1.2 $g/cm^3$, the lower limit is preferably 0.6 $g/cm^3$, more preferably 0.7 $g/cm^3$ and most preferably 0.8 $g/cm^3$, and the upper limit is preferably 1.1 $g/cm^3$, more preferably 1.0 $g/cm^3$ and most preferably 0.9 $g/cm^3$.

If the bulk density is too large, the contact area between the columnar particle and blood is too small, and the hemostatic effect is worse, and if the bulk density is too small, the columnar particle is too fluffy, resulting in that the columnar particle is washed away under the pressure of certain blood flow when the columnar particle is in contact with the blood, and the hemostasis effect becomes worse accordingly.

Preferably, the hemostatic powder is degradable in vivo, and the number of days of degradation is not more than 30 days and is more preferably not more than 15 days.

The columnar particle of the hemostatic powder contains a polymer represented by the following structural formula:

wherein
R is at least one selected from the group consisting of —NH$_2$, —OCH$_2$CH$_2$OH, —OCH$_2$CH$_2$CH$_2$OH, —OH, —ONa, —OK and —OCa;
m, n and p respectively represent number percentages of corresponding repeating units in polymer molecules, and satisfy the following equations:

$$m+n+p=1,$$

p/(m+n+p)=0.05~0.30; and the lower limit is preferably 0.10 or more, more preferably 0.15 or more, and the upper limit is more preferably 0.25 or less and more preferably 0.20 or less.

If the p value is too large, the liquid absorption amount of the particle is reduced. If the p value is too small, after the particle is in contact with the liquid, the particle is dissolved, and the shape is difficult to maintain.

When the substitution degree D is defined as =m/(m+n+p), the overall substitution degree of the particle is defined as Ds, the substitution degree of the polymer at the center point of the cross section of the particle is defined as Do, and the substitution degree of the polymer at the edge of the cross section of the particle is defined as Dx, the following equations is satisfied:
the overall substitution degree of the particle Ds=0.09~0.8, and $$Do/Dx=0~0.7.$$

The lower limit of Ds is preferably 0.2 or more, more preferably 0.3 or more and more preferably 0.4 or more, and the upper limit is preferably 0.7 or less, more preferably 0.6 or less and more preferably 0.5 or less.

If the value of Ds is too large, it is not conducive to maintaining the shape of the particle, and if the value of Ds is too small, the liquid absorption amount of the particle is reduced.

The lower limit of Do/Dx is preferably 0.05 or more, more preferably 0.1 or more and most preferably 0.15 or more, and the upper limit is preferably 0.6 or less, more preferably 0.5 or less and most preferably 0.4 or less.

If the Do/Dx is too large, the particle is dissolved in contact with the liquid, so that the basic shape of the particle cannot be maintained, which affects the use performance of the particle and is not conducive to the removal from the wound. When the substitution degree is too small, the ratio of the expansion ratio of the particle diameter/the expansion ratio of the particle length is insufficient, so that the liquid absorption amount of the particle is reduced, meanwhile the particle is adhered with the wound easily, thereby being disadvantageous for removal from the wound.

The smaller the value of Do is, the better the central shape of the particle is maintained, and the more easily the central part acts as a skeleton. For example, Do may be 0.02 or less, 0.05 or less, 0.1 or less, 0.2 or less, 0.25 or less, 0.3 or less or 0.35 or less.

The center point of the particle in the present invention is a geometric center of the cross section when the cross section of the particle is in a regular shape, and is a geometric gravity center of the cross section when the cross section of the particle is in an irregular shape.

The edge of the particle in the present invention refers to a position on the cross section of the particle farthest from the center point of the particle.

The shape of the cross section of the particle is not particularly limited. For example, it may take a circular shape, an elliptical shape, a clover shape, a four-leaf clover shape, a triangular shape, a polygonal shape or the like, but the circular shape or the elliptical shape is preferred from the viewpoint of uniform modification, and is most preferably the circular shape. The diameter of the cross section of the particle is not particularly limited, but is preferably 1-1000 μm, the lower limit is preferably 5 μm or more, more preferably 10 μm or more and most preferably 15 μm or more, and the upper limit is preferably 500 μm or less, more preferably 200 μm or less and most preferably 100 μm or less.

The length of the fiber serving as the raw material is not particularly limited, but is preferably 1-10 cm, the lower limit is preferably 2 cm or more, more preferably 3 cm or more and most preferably 5 cm or more, and the upper limit is preferably 9 cm or less, more preferably 8 cm or less and most preferably 7 cm or less. If the fiber is too short, when the fiber is pulverized and cut, the cut direction of the fiber is likely to deviate from an ideal section direction. If the fiber is too long, the fiber is likely to be entangled and lapped in the cutting and pulverizing process, so that the proportion of the ideal columnar particles in the product is reduced.

The polymer used in the particle, as shown in the above formula, has three repeating units with different structures, but the molecular formula only indicates the category of the repeating unit in the polymer, and the arrangement sequence of these repeating units may be arbitrary. In other words, as long as the proportion of these repeating units conforms to the requirements of the present invention, the arrangement sequence thereof does not affect the invention object.

The viscosity average molecular weight of the polymer of the present invention is preferably 50,000 to 10,000,000, the lower limit is preferably 100,000 or more, more preferably 200,000 or more, even more preferably 500,000 or more and most preferably 1,000,000 or more, and the upper limit is preferably 9,000,000 or less, more preferably 8,000,000 or less, even more preferably 7,000,000 or less and most preferably 6,000,000 or less.

When the viscosity average molecular weight is too large, a molecular chain is in a curled state, reaction groups on the molecular chain are easily wrapped, which is not conducive to the reaction, and the overall substitution degree is too low. When the viscosity average molecular weight is too small, the molecular chain is short, the reaction group is exposed easily, a reaction reagent and a hydrolysis reagent are more likely to penetrate through the gap the molecular chain and react with it, so that the overall substitution degree is greatly increased, and the difference between the degrees of substitution at the center point and at the edge of the cross section of the particle is small, such that the particle is dissolved after in contact with the liquid, the shape of the particle cannot be maintained, and the use performance of the particle is affected.

The group R of the polymer is preferably two or more, different moieties that is, R comprises at least R1 and R2, and more preferably R is only R1 and R2.

R1 is at least one moiety selected from the group consisting of —NH$_2$, —OCH$_2$CH$_2$OH and —OCH$_2$CH$_2$CH$_2$OH, and R2 is at least one moiety selected from the group consisting of —OH, —ONa, —OK and —OCa.

Relative to the overall content of R, the content of R1 is preferably 0-95%, the lower limit is preferably 5% or more, more preferably 10% or more and most preferably 20% or more, and the upper limit is preferably 90% or less, more preferably 80% or less and most preferably 70% or less.

Relative to the overall content of R, the content of R2 is preferably 5-100%, the lower limit is preferably 10% or more, more preferably 20% or more and most preferably 30% or more, and the upper limit is preferably 90% or less, more preferably 80% or less and most preferably 70% or less.

Preferably, the fiber serving as the raw material has good liquid absorption capacity. With reference to absorption of physiological saline (0.9% sodium chloride solution), the liquid absorption amount is preferably twice or more, more preferably 5 times or more and most preferably 10 times or more of the weight of the fiber itself (dry weight). The upper limit is not particularly limited, but when the liquid absorption amount is too high, adverse affects are generated to the shape maintenance of the fiber. It is preferably 20 times or less.

Correspondingly, as a finished product of hemostatic powder, the amount of absorbed physiological saline containing 0.9% sodium chloride is preferably 5 to 40 times of the dry weight of the hemostatic powder. As a powder, the liquid absorption capacity of the hemostatic powder is enhanced due to the increased superficial area. At the same time, as long as the hemostatic powder forms gel after absorbing liquid, maintains the state of not being dissolved into liquid, the requirement for maintaining shape is not as high as that of the whole fiber (for example, the fiber may be broken if absorbing too much liquid, and thus cannot be taken out intact, or the shape of the texture cannot be maintained, resulting in inconvenience of the operation, but such requirement is unnecessary for the hemostatic powder, as long as the hemostatic powder is not completely dissolved, even if it becomes paste or suspension, it still works), and thus absorbs more liquid than fiber. For example, although the preferred upper limit of the liquid absorption of fiber is about 20 times of its dry weight, the upper limit of the liquid absorption of the hemostatic powder can preferably be increased to about 40 times of its dry weight.

More preferably, when the particle absorbs liquid and swell, the particle only becomes thicker rather than longer as much as possible, that is, the expansion ratio of the diameter of the particle is much greater than the expansion ratio of the length of the particle, and preferably, the expansion ratio of the diameter of the particle/the expansion ratio of the length of the particle is greater than 5 times, more preferably greater than 10 times, more preferably greater than 20 times and more preferably greater than 30 times. The greater this ratio is, the better for the maintenance of the particle shape, that is, the original molecular structure is not completely dissolve or dissipated by the absorbed liquid during liquid absorption and swelling.

The diameter of the particle of the present invention means that when the cross section of the particle is a circular, the diameter of the particle is the diameter of the circle, and when the cross section of the particle is not a circle, the diameter of the particle is a line between two points having the largest distance on the edge of the cross section of the particle.

The expansion ratio of the length of the particle refers to:

(the length of the particle after liquid absorption−the length of the particle before liquid absorption)/the length of the particle before liquid absorption×100%

The expansion ratio of the diameter of the particle refers to:

(the diameter of the particle after liquid absorption−diameter of the particle before liquid absorption)/diameter of the particle before liquid absorption×100%

Examples

1. Since after the fiber is chopped, the ability of the powder to maintain particle shape is not as good as that of the fiber, the powder particles are attached to each other after absorbing liquid and are not easily separated from each other. Further testing of some parameters of the powder is not as convenient as testing the fiber itself. Therefore, when a picture of the liquid absorption performance is displayed and the data of the substitution degree distribution are measured, the liquid absorption fiber is still used, the hemostatic powder is mainly used for measuring liquid absorption amount data and the actual application effect. For most chemical properties, physically cutting fibers on approximate section direction does not affect the internal structure of the fiber, the substitution degree distribution, and the like.

Parameter Measurement Method of the Fiber Material 1.1 Measurement of m, n and p Model number of the instrument used in the measurement: nuclear magnetic resonance spectrometer of the German Bruker company with a model number AMX600M NMR The required content relationship can be calculated according to measured values, such as m/(m+n+p), p/(m+n+p) and the like.

The specific operation method is as follows: dissolving the fiber in D$_2$O of 1% CD3COOD, wherein D is deuterium so as to allow easier detection measuring proton peak areas of characteristic groups (for example, —NCH$_2$—, —OCH$_2$— in the repeating unit corresponding to m; and —NCOCH$_3$— in the repeating unit corresponding to p) of the repeating units, and calculating the proportions of the repeating units according to the proportions of the areas thereof.

1.2 Measurement of the Substitution Degree of a Certain Point (for Example, the Point at the Center or on the Edge) on the Cross Section of the Fiber The liquid absorption fiber is placed in a water/ethanol (v/v=20/80) solution containing 30% (w/v) KOH and is soaked at 60° C. for 5 hours. Then the liquid absorption fibers are taken out, repeatedly washed with 80% (v/v) ethanol aqueous solution 8 times and is dried at 40° C. for 24 hours after the washing liquid is removed. The dried fiber is quenched in liquid nitrogen, the K content of the center point of the cross section of the fiber and the K content of the edge of the fiber are measured by using an energy dispersive spectrometer (EDS). The substitution degree of each point is calculated according to this content, and the ratio of the K content of the center point of the cross section of the fiber to the K content of the edge of the fiber is the ratio of the degrees of substitution.

1.3 Liquid Absorption Performance Test
1.3.1 Liquid Absorption Amount 20 liquid absorption fibers are taken, and the dry weight is measured as W (g) by using an analytical balance. Nylon cloth is immersed in physiological saline 0.9% sodium chloride for 30 minutes and is dried after being taken out. The fiber is wrapped with the nylon cloth and is weighed as $W_1(g)$. A sufficient amount of physiological saline containing the 0.9% sodium chloride which is 500 times the weight of the 20 fibers is weighed, the fiber wrapped with the nylon cloth is placed in the physiological saline for 30 min at 37° C. The nylon cloth bag is then taken out, dried and is weighed as $W_2(g)$. The liquid absorption amount of a single fiber is $(W_2-W_1)/W$.

1.3.2 the Ratio of the Expansion Ratios of the Diameter and the Length of the Fiber The dried fiber is taken out and is fixed on a glass piece, and the diameter of the fiber and the length of the fiber after liquid absorption are measured under a microscope. Further, a dry fiber is taken and is fixed on the glass piece, and the diameter and length of the dry fiber are measured under the microscope.

The measurement results of the above data are summarized in table 1 and table 2 below.

The measurement method of the viscosity average molecular weight. The Ubbelohde viscosity method is used. A certain amount of fibers is taken and is dissolved in 0.1 mol·L$^{-1}$ CH$_3$COOH-0.2 mol·L$^{-1}$ NaCl, and an outflow time of the fiber is measured by a Ubbelohde viscometer in a constant temperature water bath of $(25\pm0.05)$ °C. so as to calculate the viscosity average molecular weight.

2. Parameter Measurement Method of Hemostatic Powder
2.1 Liquid Absorption Amount A certain amount of hemostatic powder is taken, and the dry weight is measured as W (g). Nylon cloth is immersed in physiological saline of 0.9% sodium chloride for 30 minutes and is dried after being taken out, and the powder is wrapped with the nylon cloth and is weighed as $W_1(g)$. Physiological saline containing the 0.9% sodium chloride which is 400 times the weight of the hemostatic powder is weighed, the hemostatic powder wrapped with the nylon cloth is placed in the physiological saline and is placed for 30 min at 37° C., the nylon cloth bag is then taken out, dried and is weighed as $W_2(g)$. The liquid absorption amount of the hemostatic powder in the physiological saline is $(W_2-W_1)/W$.

2.2 the Particle Diameter, Distribution and the Ratio of Long Diameter to Short Diameter of the Hemostatic Powder are Measured by Photographs Taken by a Scanning Electron Microscopy.

2.3 Bulk Density Test

The hemostatic powder is free dropped into a measuring cylinder having a volume of V(cm$^3$) and a mass of $m_0$(g) and is weighed as m, and then the bulk density $BD=(m-m_0)/V$, g/cm$^3$.

2.4 In Vivo Degradation Absorption Test

The hemostatic powder with a dry weight of $m_0$(g) is placed in a polymethyl methacrylate microporous membrane bag, weighed and marked as $m_1$(g).

The in vivo degradation test adopts a rat liver embedding material degradation model.

24 SPF grade Sprague Dawley male rats were used in experiments. Two days before the experiment, the rats are depilated with a sodium sulfide solution. Intraperitoneal injection of 3% sodium pentobarbital (30 mg/kg) is performed for anesthesia during the experiment.

After the rat is completely anesthetized, the rat is fixed on an experimental rate plate lying supine, and the limbs and the head are fixed. The abdomen of the rat is disinfected with 75% alcohol and medical iodophor, skin and muscles of abdomen are cut open right in the middle of the upper abdomen. The incision is about 5 cm, the parietal peritoneumis cut open to exposed the left lobe of the liver, and iodophor-impregnated gauze is placed below the left lobe of the liver. A piece of liver tissue of 1 cm (length)×1 cm (width)×0.3 cm (thickness) is cut from the outer edge of the left lobe of the liver to form an acute hemorrhagic wound of the liver. After free bleeding of the wound for 10 s, the surface of the wound edge is immediately wrapped by the polymethyl methacrylate microporous membrane bag, the material is taken out after gentle pressing, the bleeding condition of the wound is observed after gentle pressing for 1 min, and the pressing is repeated until the wound stops active bleeding. Subsequently, stitch the wound perpendicularly to the membrane bag and the left lobe of the liver by using absorbable sutures, the membrane bag is fixed on the wound of the liver. After no active bleeding is observed, the enterocoelia is stitched by interrupted suture by multilayer. The abdomen is disinfected again with the iodophor. After sterile gauze is applied on the sutured incision site, an elastic bandage is used for fixation of the gauze with proper pressure, and then the rats are raised in separated cages. The bandage is removed on the 2nd day after this surgery, and the survival rate of the rats are recorded. The activity condition of the rats is observed daily after the surgery. At the time points of the 7th, 14th, 21st and 28th day, 6 rats are taken, their enterocoelias are opened, the membrane bags are taken out, freeze dried and weighed as $m_2$(g). The degradation absorption ratio is $(m_1-m_2)/m_0$.

2.5 Hemostatic Performance Test

A hemostasis study is performed using a rabbit femoral arterial hemostasis model.

12 healthy New Zealand rabbits 3 months old are taken, in which half are male and half are female, and the weights are 2.5 kg. The rabbits are randomly divided into a negative control group (ordinary gauze) and an experimental group (hemostatic powder, CCS). Each group contains 6 rabbits. Two days before the experiment, the inner sides of both thighs of the rabbit are depilated with a sodium sulfide solution. 3% sodium pentobarbital (30 mg/kg) is slowly injected into the ear veins of the rabbits. After anesthesia the rabbits are lying supine, and their limbs are properly fixed on the fixing frame on operating table. The depilated area on the inner side of the left thigh are disinfected by regular iodine and alcohol, and a surgical drape is attached. A incision with a length of about 5 cm is drawn on the middle of the inner side of the left thigh along the femoral artery, the skin is cut open and is sharply separated layer by layer. The femoral artery, the femoral vein and the nervus femoralis are carefully peeled off after the femoral vascular nerve is exposed, the femoral artery is penetrated by a silk yarn, marked and properly protected, then a distal end and a proximal end are respectively clipped with blood vessel clips, and then the femoral artery is cut by ⅓ of the diameter of the blood vessel in a wedge shape. The blood vessel clip at the proximal end is released. It can be seen that the blood sprays out from the opening of the femoral artery. The femoral artery is respectively covered with 500 mg different hemostatic materials (i.e., ordinary gauze or hemostatic powder), and then is covered with 4 cm×4 cm size sterile gauze and is pressed at a constant pressure for hemostasis. The bleeding condition of the wound is observed every 20 s after 2 minutes of pressing until the bleeding stops, and if the wound no longer bleeds in 5 minutes, then a successful hemostasis is recorded. Then the hemostasis time and the blood loss amount are recorded.

Embodiment 1

5 g of chitin fibers with a length of 6 cm and p/(m+n+p) of 0.25 are weighed and are dispersed in 50 mL of isopropanol, 2.54 g of 2-hydroxyethyl acrylate is added and is shaken to a uniform solution at room temperature. A reaction is carried out at a constant temperature water bath for 48 hours at 50° C., and the chitin fibers are separated from the reaction mixed solution after the reaction and are washed twice with a 80% (v/v) methanol aqueous solution. The fibers are taken out, dried and are dispersed in the 80% (v/v) methanol aqueous solution, a 30% (w/v) potassium hydroxide aqueous solution is dripped in, the pH of a mixed solution of the methanol aqueous solution and the potassium hydroxide aqueous solution is adjusted to 11.0, the fibers are soaked for 1 hour, the soaked fibers are separated from the mixed solution and are washed with the 80% (v/v) methanol aqueous solution three times, and the fibers are dried at 40° C. after being dehydrated to obtain liquid absorption fibers having a viscosity average molecular weight (Mη) of 3,000,000 and a substitution degree of an acryloyl group of 0.17 by the overall amount of substance.

The liquid absorption fiber is dissolved in 1% CD3COOD solution of $D_2O$, the proton peak areas of —$NCH_2$— and —$OCH_2$— are respectively measured by nuclear magnetic resonance spectrometry, and then by calculation, in the substituted acryloyl group, the content of R2, namely —OK, is 22%; and the content of R1, namely —$OCH_2CH_2OH$, is 78%.

Embodiment 2

5 g of chitin fibers with a length of 6 cm and p/(m+n+p) of 0.10 are weighed and are dispersed in 50 mL of isopropanol, 7.09 g of 2-hydroxyethyl acrylate is added and is shaken to uniform solution at room temperature, a reaction is carried out in a constant temperature water bath for 48 hours at 70° C., and the chitin fibers are separated from the reaction mixed solution after the reaction, and are washed twice with a 80% (v/v) methanol aqueous solution, the fibers are taken out, dried and are dispersed in the 80% (v/v) methanol aqueous solution, a 30% (w/v) potassium hydroxide aqueous solution is dripped in, the pH of a mixed solution of the methanol aqueous solution and the potassium hydroxide aqueous solution is adjusted to 11.0, the fibers are soaked for 1 hour, the soaked fibers are separated from the mixed solution and are washed with the 80% (v/v) methanol aqueous solution for three times, and the fibers are dried at 40° C. after being dehydrated to obtain liquid absorption fibers having a viscosity average molecular weight of 3,000,000 and a substitution degree of an acryloyl group of 0.30 by overall amount of substance.

The liquid absorption fiber is dissolved in 1% CD3COOD solution of $D_2O$, and the proton peak areas of —$NCH_2$— and —$OCH_2$— are respectively measured by nuclear magnetic resonance spectrometry, and then by calculation, in the substituted acryloyl group, the content of R2, namely —OK, is 35%; and then the content of R1, namely —$OCH_2CH_2CH_2OH$, is 65%.

Embodiment 3

5 g of chitin fibers with a length of 6 cm and p/(m+n+p) of 0.10 are weighed and are dispersed in 50 mL of isopropanol, 14.17 g of 2-hydroxyethyl acrylate is added and is shaken to uniform solution at room temperature, a reaction is carried out in a constant temperature water bath for 48 hours at 70° C., and the chitin fibers are separated from the reaction mixed solution after the reaction and are washed twice with a 80% (v/v) methanol aqueous solution, the fibers are taken out, dried and are dispersed in the 80% (v/v) methanol aqueous solution, a 30% (w/v) potassium hydroxide aqueous solution is dripped in, the pH of a mixed solution of the methanol aqueous solution and the potassium hydroxide aqueous solution is adjusted to 11.5, the fibers are soaked for 1 hour, the soaked fibers are separated from the mixed solution, are dried and are placed in a saturated $CaCl_2$) solution to be soaked for 1 hour, the fibers are taken out and are washed with the 80% (v/v) methanol aqueous solution for three times, and the fibers are dried at 40° C. after being dehydrated to obtain liquid absorption fibers having a viscosity average molecular weight of 500,000 and a substitution degree of an acryloyl group of 0.49 by the overall amount of substance.

The liquid absorption fiber is dissolved in 1% CD3COOD solution of $D_2O$, and the proton peak areas of —$NCH_2$— and —$OCH_2$— are respectively measured by nuclear magnetic resonance spectrometry, and then by calculation, in the substituted acryloyl group, the content of R2, namely —OCa, is 39%; and the content of R1, namely —$OCH_2 CH_2 CH_2OH$, is 61%.

Embodiment 4

5 g of chitin fibers with a length of 6 cm and p/(m+n+p) of 0.25 are weighed and are dispersed in 50 mL of isopropanol, 5.08 g of 2-hydroxyethyl acrylate is added and is shaken to uniform solution at room temperature, a reaction is carried out in a constant temperature water bath for 58 hours at 55° C., and the chitin fibers are separated from the reaction mixed solution after the reaction and are washed twice with a 80% (v/v) methanol aqueous solution, the fibers are taken out, dried and are dispersed in the 80% (v/v) methanol aqueous solution, a 30% (w/v) potassium hydroxide aqueous solution is dripped in, the pH of a mixed solution of the methanol aqueous solution and the potassium hydroxide aqueous solution is adjusted to 11.5, the fibers are soaked for 1 hour, the soaked fibers are separated from the mixed solution, are dried and are placed in a saturated $CaCl_2$ solution to be soaked for 1 hour, the fibers are taken out and are washed with the 80% (v/v) methanol aqueous solution for three times, and the fibers are dried at 40° C. after being dehydrated to obtain liquid absorption fibers having a viscosity average molecular weight of 500,000 and a substitution degree of an acryloyl group of 0.55 by the overall amount of substance.

The liquid absorption fiber is dissolved in 1% CD3COOD solution of $D_2O$, and the proton peak areas of —$NCH_2$— and —$OCH_2$— are respectively measured by nuclear magnetic resonance spectrometry, and then by calculation, in the substituted acryloyl group, the content of R2, namely —OCa, is 27%; and the content of R1, namely —$OCH_2 CH_2 CH_2OH$, is 73%.

Embodiment 5

5 g of chitin fibers with a length of 6 cm and p/(m+n+p) of 0.25 are weighed and are dispersed in 50 mL of isopropanol, 6.30 g of acrylic acid is added and is shaken to uniform solution at room temperature, a reaction is carried out in a constant temperature water bath for 40 hours at 70°

C., and the chitin fibers are separated from the reaction mixed solution after the reaction and are washed twice with a 80% (v/v) methanol aqueous solution, the fibers are taken out, dried and are washed with the 80% (v/v) methanol aqueous solution for three times, and the fibers are taken out and are dried at 40° C. after being dehydrated to obtain liquid absorption fibers having a viscosity average molecular weight of 80,000 and a substitution degree of an acryloyl group of 0.75 by the overall amount of substance.

The liquid absorption fiber is dissolved in 1% CD3COOD solution of $D_2O$ to perform a nuclear magnetic resonance spectrum test. The result indicates that, compared with the chitin fiber raw material, the liquid absorption fiber only has two new absorption peaks at chemical shifts of 2.3 and 3.1, which belong to —$NCH_2CH_2CO$—, indicating that the content of R2, namely, —OH is 100%, and meanwhile, the substitution degree of the overall amount of substance of an acryloyl group can be calculated as 0.75.

Embodiment 6

5 g of chitin fibers with a length of 6 cm and p/(m+n+p) of 0.10 are weighed and are dispersed in 50 mL of isopropanol, 1.91 g of acrylamide is added and is shaken to uniform solution at room temperature, a reaction is carried out in a constant temperature water bath for 72 hours at 40° C., and the chitin fibers are separated from reaction mixed solution after the reaction and are washed twice with a 80% (v/v) methanol aqueous solution, the chitin fibers are taken out and are placed in a saturated sodium bicarbonate solution at 40° C. to be soaked for 1 hour after being dried, the fibers are taken out and are washed with the 80% (v/v) methanol aqueous solution for three times, and the fibers are dried at 40° C. after being dehydrated to obtain liquid absorption fibers having a viscosity average molecular weight of 9,000,000 and a substitution degree of an acryloyl group of 0.09 by the overall amount of substance.

The liquid absorption fiber is dissolved in 1% dilute acetic acid, and it is tested by a sodium ion meter, as a result, in the substituted acryloyl group, the content of R2, namely —OCa, is 5%; and the content of R1, namely —$NH_2$, is 95%.

The liquid absorption fiber is quenched in liquid nitrogen, and the contents of —CO— of the center point of the cross section of the fiber and the edge of the fiber are measured by X-ray photoelectron spectroscopy (XPS), so that the degrees of substitution of acryloyl groups at the center point of the cross section of the fiber and the edge of the fiber are respectively calculated as 0 and 0.12.

TABLE 1

Basic parameters of the fiber

| Embodiment | p/(m + n + p) | Mη | m/(m + n + p) (Ds) | Potassium content at the center (%) | Potassium content at the edge (%) | Do/Dx | Substitution degree at the center Do | Substitution degree at the edge Dx |
|---|---|---|---|---|---|---|---|---|
| 1 | 0.25 | 3,000,000 | 0.17 | 1.10 | 6.13 | 0.15 | 0.05 | 0.33 |
| 2 | 0.10 | 3,000,000 | 0.30 | 4.94 | 6.63 | 0.70 | 0.25 | 0.36 |
| 3 | 0.10 | 500,000 | 0.49 | 5.89 | 8.85 | 0.58 | 0.31 | 0.53 |
| 4 | 0.25 | 500,000 | 0.55 | 6.44 | 11.71 | 0.44 | 0.35 | 0.79 |
| 5 | 0.25 | 80,000 | 0.75 | 4.96 | 15.15 | 0.26 | 0.24 | 0.92 |
| 6 | 0.10 | 9,000,000 | 0.09 | — | — | 0 | 0 | 0.12 |

In the above table, the calculation process of each embodiment is as follows:

The degrees of substitution of the acryloyl groups at different sites of the cross section of the fiber are tested by EDS, that is, the liquid absorption fiber is completely hydrolyzed to potassium carboxylate by a KOH solution, after thorough cleaning and drying, the amount of the substance of K is equal to the amount of the substance of the carboxylate, the content of K is tested by the EDS, and then the amount of the substance of the carboxylate can be calculated and then the substitution degree of the acryloyl group can be calculated.

For the embodiment 6, since the grafted acrylamide cannot generate a carboxyl group by hydrolysis, the —CO— content is obtained by an XPS test so as to calculate the degrees of substitution at different sites.

TABLE 2

Liquid absorption performance of the fiber

| Embodiment = | Diameter of the fiber (μm) | Length of the fiber (cm) | Diameter of the fiber after liquid absorption (μm) | Length of the fiber after liquid absorption (cm) | Expansion ratio of the diameter (%) | Length Expansion ratio (%) | Diameter expansion ratio/length expansion ratio (multiple) | Liquid absorption amount (multiple) |
|---|---|---|---|---|---|---|---|---|
| 1 | 100 | 6.0 | 210 | 6.7 | 110 | 11.7 | 9.4 | 4.2 |
| 2 | 15 | 6.0 | 38 | 6.7 | 153 | 11.7 | 13.1 | 8.9 |
| 3 | 20 | 6.0 | 55 | 6.8 | 175 | 13.3 | 13.2 | 13.5 |
| 4 | 20 | 6.0 | 62 | 6.7 | 210 | 11.7 | 17.9 | 17.8 |
| 5 | 5 | 6.0 | 25 | 6.7 | 400 | 11.7 | 34.2 | 20.0 |
| 6 | 100 | 6.0 | 168 | 6.8 | 68 | 13.3 | 5.1 | 2.0 |

Comparative Example

A series of fibers with the same substitution degree ($D_0/D_x=1$) from the center point of the cross section of the fiber to the edge of the fiber are prepared, and the shape after the liquid absorption of the fibers is tested by the following method, and the fiber shape maintenance states of the fibers after contacting with liquid are observed.

8.3 g of NaCl and 0.277 g of $CaCl_2$ are weighed and are fully dissolved in distilled water, the solution is placed in a volumetric flask, the volume is adjusted to 1000 mL by using distilled water, and the obtained solution is an A solution specified in the British Pharmacopoeia. The solution simulates the content of major metal ions in human blood.

Shape Comparison of the Fiber after Liquid Absorption 1 fiber is taken, both ends are fixed on a glass piece with double-sided tapes, 0.25 mL of A solution is dripped on the middle of the fiber, the fiber is placed at 37° C. for 30 min and is then taken out, and the shape change of the fiber after the liquid absorption is observed under an optical microscope.

TABLE 3

Liquid absorption performance measurement of the fiber

| Comparative example | $p/(m+n+p)$ | $M\eta$ | $m/(m+n+p)$ (Ds) | $D_0/D_x$ | Liquid absorption amount (multiple) |
|---|---|---|---|---|---|
| 1 | 0.25 | 80,000 | 0.70 | 1 | Cannot be measured |
| 2 | 0.25 | 3,000,000 | 0.18 | 1 | 3.5 |

As a result, the fiber of the comparative example 1 is difficult to maintain a complete shape, and thus it is difficult to accurately measure the liquid absorption amount. Although the liquid absorption amount can be measured in the comparative example 2, but the liquid absorption thereof is lower than that of the present invention, it is presumed that under the same substitution degree, although the microscopic shape of the uniformly substituted fiber is maintained after the liquid absorption, compared with the present invention, the structure is loose, and a small amount is dissolved, so that the binding force to water is not strong enough, and a part of water that is not combined with the fiber firmly is lost after spin drying and drying.

An airflow pulverizing treatment is performed on the fibers of the embodiments 1 to 6 and the comparative examples 1 and 2 for 30 minutes to obtain the hemostatic powder of embodiments 7-12 and comparative examples 3 and 4, and the test results are as follows.

TABLE 4

Parameters and liquid absorption performance of the hemostatic powder

| Embodiment | Particle diameter (μm) | Length to diameter ratio | Bulk density (g/cm³) | Liquid absorption amount (g/g) |
|---|---|---|---|---|
| 7 | 0.2~2.2 | 0.87 ± 0.02 | 1.20 ± 0.01 | 18.1 ± 0.1 |
| 8 | 1.1~4.7 | 0.92 ± 0.02 | 1.02 ± 0.03 | 19.0 ± 0.2 |
| 9 | 4.3~10.5 | 0.89 ± 0.04 | 0.71 ± 0.03 | 31.5 ± 0.1 |
| 10 | 15.4~40.9 | 0.95 ± 0.01 | 0.48 ± 0.05 | 40.0 ± 0.1 |
| 11 | 23.6~48.9 | 0.97 ± 0.06 | 0.50 ± 0.04 | 35.7 ± 0.2 |
| 12 | 19.6~51.5 | 0.99 ± 0.05 | 0.55 ± 0.05 | 5.0 ± 0.1 |

TABLE 4-continued

Parameters and liquid absorption performance of the hemostatic powder

| Embodiment | Particle diameter (μm) | Length to diameter ratio | Bulk density (g/cm³) | Liquid absorption amount (g/g) |
|---|---|---|---|---|
| Comparative example 1 | 20.0~47.2 | 0.98 ± 0.03 | 0.51 ± 0.04 | Cannot be measured |
| Comparative example 4 | 23.1~49.1 | 0.98 ± 0.01 | 0.53 ± 0.02 | 3.5 ± 0.2 |

TABLE 5

In vivo degradation absorption performance test of the hemostatic powder

| Embodiment | \multicolumn{4}{c}{Degradation absorption time} |
| | 7 | 14 | 21 | 28 |
| | \multicolumn{4}{c}{$(m_1-m_2)/m_0$} |

| Embodiment | 7 | 14 | 21 | 28 |
|---|---|---|---|---|
| 7 | 0.28 ± 0.02 | 0.61 ± 0.09 | 0.89 ± 0.05 | 1.00, no visible implant in the membrane bag |
| 8 | 0.49 ± 0.03 | 0.79 ± 0.08 | 1.00, no visible implant in the membrane bag | |
| 9 | 0.62 ± 0.14 | 1.00, no visible implant in the membrane bag | | |
| 10 | 0.69 ± 0.12 | 1.00, no visible implant in the membrane bag | | |
| 11 | 0.45 ± 0.04 | 0.96 ± 0.15 | 1.00, no visible implant in the membrane bag | |
| 12 | 0.28 ± 0.07 | 0.49 ± 0.06 | 0.78 ± 0.14 | 0.99 ± 0.07 |
| Comparative example 3 | 1.00 | 1.00 | 1.00 | 1.00 |
| Comparative example 4 | 0.29 ± 0.03 | 0.48 ± 0.07 | 0.75 ± 0.15 | 0.90 ± 0.06 |

In the animal hemostasis experiment, the hemostasis time of the hemostatic powder of the present invention is 225 seconds, which is significantly lower than the 698 seconds of the ordinary gauze. The result indicates that the hemostatic powder has a significant hemostatic effect on the rabbit femoral arterial bleeding.

The invention claimed is:

1. A hemostatic powder, comprising columnar particles, wherein the columnar particles have a axial length/diameter ratio of less than 5;

wherein said hemostatic powder comprises a polymer represented by the following structural formula:

-continued wherein
R is at least one moiety selected from the group consisting of —$NH_2$, —$OCH_2CH_2OH$, —$OCH_2CH_2CH_2OH$, —OH, —ONa, —OK and/or —OCa;

m, n and p respectively represent numerical percentages of corresponding repeating units in the molecule of the polymer, and satisfy the following equations:

$$m+n+p=1,$$

$$p/(m+n+p)=0.05\sim0.30;$$

wherein said polymer has a substitution degree D is defined as D=m/(m+n+p), and said columnar particles have an overall substitution degree is defined as Ds, and the polymer has a substitution degree at a center point of a cross section of said columnar particles defined as Do, and a substitution degree of at an edge of a cross section of said columnar particles is defined as Dx, and the following equations are satisfied:

$$Ds=0.09\sim0.8,$$

$$Do/Dx=0\sim0.7.$$

2. The hemostatic powder according to claim 1, wherein R is $R_1$ and $R_2$, wherein $R_1$ is from 0 to 95% of $R_1$ and $R_2$ is from 5 to 100% of $R_1$,
wherein
R1 is at least one moiety selected from the group consisting of —$NH_2$, —$OCH_2CH_2OH$ and —$OCH_2CH_2CH_2OH$,
and R2 is at least one moiety selected from the group consisting of —OH, —ONa, —OK and —OCa.

3. The hemostatic powder according to claim 1, wherein Ds=0.2-0.7.

4. The hemostatic powder according to claim 1, wherein Ds=0.3-0.6.

5. The hemostatic powder according to claim 1, wherein Ds=0.4-0.5.

6. The hemostatic powder according to claim 1, wherein Do/Dx=0-0.6.

7. The hemostatic powder according to claim 1, wherein Do/Dx=0-0.5.

8. The hemostatic powder according to claim 1, wherein Do/Dx=0-0.4.

9. The hemostatic powder according to claim 1, wherein the polymer has a viscosity average molecular weight Mη in a range of 50, 000-10,000,000.

10. The hemostatic powder according to claim 1, wherein the hemostatic powder has a liquid absorbing amount of 5 to 40 times of the dry weight of said powder when it absorbs physiological saline solution containing 0.9% sodium chloride.

11. The hemostatic powder according to claim 1, wherein after the hemostatic powder absorbs liquid, the hemostatic powder has an expansion percentage along radial direction of the particles of more than 5 times of an expansion percentage along axial direction of the particles,
wherein the radial direction means a direction of a connecting line from the center of the cross section of the particles to the edge of the cross section of the particles, and
the axial direction means a direction vertical to the cross section of the particles.

12. The hemostatic powder according to claim 1, wherein the hemostatic powder has a particle diameter of 0.2-1000 μm.

13. The hemostatic powder according to claim 1, wherein the hemostatic powder has a ratio of axial length to diameter in a range of 0.8:1-1:0.8.

14. The hemostatic powder according to claim 1, wherein the hemostatic powder has a bulk density of 0.5-1.2 g/cm³.

15. The hemostatic powder according to claim 1, wherein the hemostatic powder has a degradation time in a human body or a mouse of less than 30 days.

16. The hemostatic powder according to claim 1, wherein the hemostatic powder is prepared by pulverizing or cutting fibers.

* * * * *

UNITED STATES PATENT AND TRADEMARK OFFICE
CERTIFICATE OF CORRECTION

PATENT NO. : 10,946,039 B2
APPLICATION NO. : 16/343887
DATED : March 16, 2021
INVENTOR(S) : Yingshan Zhou et al.

It is certified that error appears in the above-identified patent and that said Letters Patent is hereby corrected as shown below:

On the Title Page

Item (72) Inventors, should read:
Yingshan Zhou, Jiangsu (CN);
Rui Jiang, Jiangsu (CN);
Zuguang Gong, Jiangsu (CN);
Liqin XU, Jiangsu (CN);
Shiming Zhou, Jiangsu (CN);
Xiaoming Zhou, Jiangsu (CN).

Signed and Sealed this
Eighth Day of June, 2021

Drew Hirshfeld
*Performing the Functions and Duties of the
Under Secretary of Commerce for Intellectual Property and
Director of the United States Patent and Trademark Office*